(12) United States Patent
Ashibe et al.

(10) Patent No.: US 12,215,091 B2
(45) Date of Patent: Feb. 4, 2025

(54) METHOD FOR PRODUCING METHYLENE DISULFONATE COMPOUND

(71) Applicant: SUMITOMO SEIKA CHEMICALS CO., LTD., Hyogo (JP)

(72) Inventors: Seiya Ashibe, Kako-gun (JP); Hirotake Moriyama, Kako-gun (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 0 days.

(21) Appl. No.: 17/798,637

(22) PCT Filed: Feb. 8, 2021

(86) PCT No.: PCT/JP2021/004488
§ 371 (c)(1),
(2) Date: Aug. 10, 2022

(87) PCT Pub. No.: WO2021/161943
PCT Pub. Date: Aug. 19, 2021

(65) Prior Publication Data
US 2023/0150967 A1  May 18, 2023

(30) Foreign Application Priority Data
Feb. 14, 2020  (JP) ................. 2020-023222

(51) Int. Cl.
*C07D 327/00* (2006.01)
(52) U.S. Cl.
CPC ................. *C07D 327/00* (2013.01)
(58) Field of Classification Search
CPC ................................. C07D 327/00
See application file for complete search history.

(56) References Cited

U.S. PATENT DOCUMENTS

| | | | | |
|---|---|---|---|---|
| 4,046,806 A | * | 9/1977 | Kozlowski | D06M 13/252 260/DIG. 24 |
| 4,276,187 A | * | 6/1981 | Sakai | C07D 401/12 423/576.5 |
| 2003/0070928 A1 | | 4/2003 | Werninger et al. | |

FOREIGN PATENT DOCUMENTS

| | | |
|---|---|---|
| CN | 1398852 A | 2/2003 |
| CN | 108840852 A | 11/2018 |
| EP | 4 006 019 A1 | 6/2022 |
| WO | 2015/064712 A1 | 5/2015 |
| WO | 2021/015219 A1 | 1/2021 |

OTHER PUBLICATIONS

Robinson et al., Canadian Journal of Chemistry, vol. 44, 1966, pp. 1437-1444. (Year: 1966).*
International Search Report of PCT/JP2021/004488 dated Mar. 16, 2021 [PCT/ISA/210].
Office Action issued Nov. 3, 2023 by State Intellectual Property Office of China in Chinese Application No. 202180013360.3.

* cited by examiner

*Primary Examiner* — Laura L Stockton
(74) *Attorney, Agent, or Firm* — Sughrue Mion, PLLC

(57) ABSTRACT

Provided is an industrially advantageous method for producing a methylene disulfonate compound easily and inexpensively using fewer raw materials. The method for producing a methylene disulfonate compound of the present invention comprises step A of reacting at least one alkanesulfonic acid compound and sulfur trioxide in the presence of at least one member selected from the group consisting of a sulfoxide compound and a sulfone compound to thereby obtain reactant A comprising an alkanedisulfonic acid compound, and step B of reacting reactant A obtained in step A and a formaldehyde compound in the presence of sulfur trioxide to thereby obtain a methylene disulfonate compound.

4 Claims, No Drawings

METHOD FOR PRODUCING METHYLENE DISULFONATE COMPOUND

CROSS REFERENCE TO RELATED APPLICATIONS

This application is a National Stage of International Application No. PCT/JP2021/004488 filed on Feb. 8, 2021, claiming priority based on Japanese Patent Application No. 2020-023222 filed on Feb. 14, 2020.

TECHNICAL FIELD

The present invention relates to a method for producing a methylene disulfonate compound.

BACKGROUND ART

Conventionally, methylene disulfonate compounds are known to be useful not only as drugs for treating leukemia in animals, but also as raw materials for functional materials such as stabilizers for secondary battery electrolytes, and are compounds with high utility value. Such methylene disulfonate compounds are known to be produced by various methods.

As an example of the production of methylene disulfonate compounds, a method using methanesulfonic acid, which is an inexpensive raw material, is known. For example, PTL 1 discloses a technique of producing a methylene disulfonate compound by reacting methanesulfonic acid with sulfur trioxide to obtain methanedisulfonic acid (first step), and further reacting the obtained methanedisulfonic acid and paraformaldehyde in the presence of a dehydrating agent (second step).

CITATION LIST

Patent Literature

PTL 1: CN108840852

SUMMARY OF INVENTION

Technical Problem

However, the method disclosed in PTL 1 had a problem that the process tended to be complicated because different reaction raw materials were used in the first and second steps and, in addition, intermediates had to be isolated.

The present invention was made in view of the above problem, and its object is to provide an industrially advantageous method for producing a methylene disulfonate compound easily and inexpensively using fewer raw materials.

Solution to Problem

The present inventors conducted extensive research to achieve the above object, and consequently found that the above object can be achieved by using a product obtained by reacting a specific alkanesulfonic acid compound and sulfur trioxide in the presence of a specific sulfoxide compound and/or sulfone compound. Thus, the present invention has been completed.

Specifically, the present invention includes, for example, the main subjects described in the following items.

Item 1.

A method for producing a methylene disulfonate compound, comprising:
step A of reacting at least one alkanesulfonic acid compound and sulfur trioxide in the presence of at least one member selected from the group consisting of a sulfoxide compound and a sulfone compound to thereby obtain reactant A comprising an alkanedisulfonic acid compound, and
step B of reacting reactant A obtained in step A and a formaldehyde compound in the presence of sulfur trioxide to thereby obtain a methylene disulfonate compound;
the alkanesulfonic acid compound being represented by the following formula (1):

wherein in formula (1), $R^1$ and $R^2$ are the same or different, and each is a $C_{1-4}$ alkyl group optionally substituted with a halogen atom, or a hydrogen atom; and n is an integer of 1 to 4; when n is an integer of 2 to 4, n-number of $R^1$ may be the same or different, and n-number of $R^2$ may be the same or different;
the sulfoxide compound being represented by the following formula (2):

wherein in formula (2), $R^3$ and $R^4$ are the same or different, and each is a substituted or unsubstituted $C_{1-12}$ alkyl group, and $R^3$ and $R^4$ may bind to each other with or without a heteroatom together with the sulfur atom to which they bind to form a ring structure;
the sulfone compound being represented by the following formula (3):

wherein in formula (3), $R^3$ and $R^4$ are the same or different, and each is a substituted or unsubstituted $C_{1-12}$ alkyl group, and $R^3$ and $R^4$ may bind to each other with or without a heteroatom together with the sulfur atom to which they bind to form a ring structure;
the alkanedisulfonic acid compound being represented by the following formula (4):

wherein in formula (4), $R^1$, $R^2$, and n are respectively the same as $R^1$, $R^2$, and n in formula (1); and the methylene disulfonate compound being represented by the following formula (5):

wherein in formula (5), $R^1$, $R^2$, and n are respectively the same as $R^1$, $R^2$, and n in formula (1).

Item 2.

The method for producing a methylene disulfonate compound according to Item 1, wherein reactant A obtained in step A is used in step B without isolating the alkanedisulfonic acid compound from reactant A.

Item 3.

The method for producing a methylene disulfonate compound according to Item 1 or 2, wherein the reaction of step A and the reaction of step B are performed in the presence of a solvent.

Item 4.

The method for producing a methylene disulfonate compound according to Item 3, wherein the solvent comprises the compound represented by formula (3).

Item 5.

The method for producing a methylene disulfonate compound according to Item 4, wherein the compound represented by formula (3) is sulfolane.

Item 6.

The method for producing a methylene disulfonate compound according to any one of Items 1 to 5, wherein the formaldehyde compound is at least one member selected from the group consisting of paraformaldehyde, anhydrous formaldehyde, trioxane, and methylal.

Advantageous Effects of Invention

According to the production method of the present invention, it is possible to produce a methylene disulfonate compound easily and inexpensively using fewer raw materials. Therefore, the production method according to the present invention is also industrially advantageous.

DESCRIPTION OF EMBODIMENTS

Embodiments of the present invention are described in detail below. In the present specification, the term "comprising" includes "consisting essentially of" and "consisting of."

In the numerical range described in stages in the present specification, the upper or lower limit of the numerical range at one stage can be optionally combined with the upper or lower limit of the numerical range at another stage. In the numerical range described in the present specification, the upper or lower limit of the numerical range may be replaced with a value shown in the Examples or a value that can be uniquely derived from the Examples. Further, in the present specification, the numerical values connected by "to" mean the numerical range including the numerical values before and after "to" as the lower limit value and the upper limit value.

The method for producing a methylene disulfonate compound of the present invention comprises at least the following steps A and B:

step A: reacting at least one alkanesulfonic acid compound and sulfur trioxide in the presence of at least one member selected from the group consisting of a sulfoxide compound and a sulfone compound to thereby obtain reactant A comprising an alkanedisulfonic acid compound; and step B: reacting reactant A obtained in step A and a formaldehyde compound in the presence of sulfur trioxide to thereby obtain a methylene disulfonate compound.

1. Step A

In step A, at least one alkanesulfonic acid compound and sulfur trioxide are reacted in the presence of at least one member selected from the group consisting of a sulfoxide compound and a sulfone compound. As a result of this reaction, reactant A comprising an alkanedisulfonic acid compound is produced. Specifically, step A is a step for producing an alkanedisulfonic acid compound.

Alkanesulfonic Acid Compound

The alkanesulfonic acid compound used in step A is represented by the following formula (1):

In formula (1), $R^1$ and $R^2$ are the same or different, and each is a $C_{1-4}$ alkyl group optionally substituted with a halogen atom, or a hydrogen atom; and n is an integer of 1 to 4. In formula (1), when n is an integer of 2 to 4, n-number of $R^1$ may be the same or different. Further, when n is an integer of 2 to 4, n-number of $R^2$ may be the same or different.

In $R^1$ and $R^2$ of formula (1), the type of $C_{1-4}$ alkyl group optionally substituted with a halogen atom is not particularly limited. Examples of the halogen atom include a fluorine atom, a chlorine atom, a bromine atom, and the like. Specific examples of the $C_{1-4}$ alkyl group optionally substituted with a halogen atom include a methyl group, an ethyl group, an n-propyl group, an iso-propyl group, an n-butyl group, an iso-butyl group, a sec-butyl group, a tert-butyl group, a fluoromethyl group, a trifluoromethyl group, a chloromethyl group, a chloroethyl group, a chloropropyl group, a bromomethyl group, and the like.

In formula (1), $R^1$ is preferably a hydrogen atom, a methyl group, an ethyl group, or an n-propyl group; and more preferably a hydrogen atom among these. $R^2$ is preferably a hydrogen atom, a methyl group, an ethyl group, or an n-propyl group; and more preferably a hydrogen atom among these. In formula (1), $R^1$ and $R^2$ are preferably the same.

In formula (1), when n is an integer of 2 to 4, that is, when n is 2, 3, or 4, n-number of $R^1$ in the compound represented by formula (1) may be the same or different. Similarly, n-number of $R^2$ may be the same or different. In formula (1), when n is an integer of 2 to 4, all of n-number of $R^1$ in the compound represented by formula (1) are preferably the same. When n is an integer of 2 to 4, all of n-number of $R^2$ in the compound represented by formula (1) are preferably the same.

In formula (1), n is particularly preferably 1. In this case, the yield of the object alkanedisulfonic acid compound tends to be particularly high.

The alkanesulfonic acid compound is not particularly limited, as long as it is a compound represented by formula (1). Preferred examples include methanesulfonic acid (in formula (1), $R^1=R^2=H$, n=1), ethanesulfonic acid (in formula (1), $R^1=CH_3$, $R^2=H$, n=1), 1-propanesulfonic acid (in formula (1), $R^1=CH_2CH_3$, $R^2=H$, n=1), 2-propanesulfonic acid (in formula (1), $R^1=R^2=CH_3$, n=1), 1-butanesulfonic acid (in formula (1), $R^1=R^2=H$, n=4), and the like.

The alkanesulfonic acid compound used in step A can be obtained from a commercially available product, or can be obtained by a known method or a method easily conceived of from a known method. For example, with reference to Tetrahedron Letters (2009), 50(46), 6231-6232, the alkanesulfonic acid compound can be synthesized by a method of oxidizing a corresponding disulfide compound using methyltrioxorhenium(VII)/hydrogen peroxide as a catalyst. Alternatively, with reference to WO2004/058693, the alkanesulfonic acid compound can be synthesized by a method of oxidizing a corresponding thiol compound using hydrogen peroxide.

The alkanesulfonic acid compounds usable in step A can be used singly or in combination of two or more.

Sulfoxide Compound and Sulfone Compound

In step A, either or both of a sulfoxide compound and a sulfone compound can be used.

The sulfoxide compound is represented by the following formula (2):

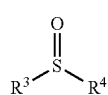

(2)

In formula (2), $R^3$ and $R^4$ are the same or different, and each is a substituted or unsubstituted $C_{1-12}$ alkyl group. In formula (2), $R^3$ and $R^4$ may bind to each other with or without a heteroatom together with the sulfur atom to which they bind to form a ring structure.

Further, the sulfone compound is represented by the following formula (3):

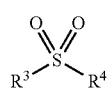

(3)

In formula (3), $R^3$ and $R^4$ are the same or different, and each is a substituted or unsubstituted $C_{1-12}$ alkyl group, and $R^3$ and $R^4$ may bind to each other with or without a heteroatom together with the sulfur atom to which they bind to form a ring structure. That is, $R^3$ and $R^4$ in formula (3) are respectively the same as $R^3$ and $R^4$ in formula (2).

In $R^3$ and $R^4$ of formulas (2) and (3), when the $C_{1-12}$ alkyl group has a substituent, the type of substituent is not particularly limited. Specific examples of substituents include a halogen atom, an alkoxy group, a carboxyl group, a cyano group, a nitro group, a sulfo group, and the like.

In $R^3$ and $R^4$ of formulas (2) and (3), examples of the $C_{1-12}$ alkyl group include a methyl group, an ethyl group, an n-propyl group, an iso-propyl group, an n-butyl group, an iso-butyl group, a sec-butyl group, a tert-butyl group, an n-hexyl group, an n-octyl group, an n-decyl group, a cyclopropyl group, a cyclobutyl group, a cyclopentyl group, a cyclohexyl group, a cyclooctyl group, a norbornyl group, an adamantyl group, a cyclopentylmethyl group, a cyclohexylmethyl group, a 2-cyclohexylethyl group, and the like. These alkyl groups may have the substituents described above. Because the yield of the object alkanedisulfonic acid compound tends to be high, the number of carbon atoms is preferably 1 to 6. Therefore, among the above examples, the $C_{1-12}$ alkyl group is preferably a methyl group, an ethyl group, an n-propyl group, an iso-propyl group, an n-butyl group, an iso-butyl group, a sec-butyl group, a tert-butyl group, an n-hexyl group, a cyclopropyl group, a cyclobutyl group, a cyclopentyl group, a cyclohexyl group, or a cyclopentylmethyl group.

In formulas (2) and (3), $R^3$ and $R^4$ may bind to each other with or without a heteroatom together with the sulfur atom to which they bind to form a ring structure. That is, $R^3$ and $R^4$ may form a ring structure containing the sulfur atoms in the compounds represented by formulas (2) and (3) as ring members. In this case, for example, the carbon atoms in $R^3$ and $R^4$ can form chemical bonds to form a ring structure. For example, covalent bonds between the terminal carbon atoms in $R^3$ and $R^4$ can form a ring structure with the sulfur atoms. The ring structure is, for example, a saturated ring containing a sulfur atom. When the ring structure has a heteroatom in addition to the sulfur atom, the type of heteroatom is not particularly limited.

When the compound represented by formula (2) and the compound represented by formula (3) are both used in step A, $R^3$ in formula (2) and $R^3$ in formula (3) may be the same or different. Similarly, when the compound represented by formula (2) and the compound represented by formula (3) are both used in step A, $R^4$ in formula (2) and $R^4$ in formula (3) may be the same or different.

Specific examples of the sulfoxide compound represented by formula (2) include dimethylsulfoxide, ethylmethylsulfoxide, methyl n-propylsulfoxide, dipropylsulfoxide, dibutylsulfoxide, di-n-octylsulfoxide, didodecylsulfoxide, tetramethylenesulfoxide, and the like. Among these, the sulfoxide compound represented by formula (2) is preferably dimethylsulfoxide.

Specific examples of the sulfone compound represented by formula (3) include trimethylene sulfone, hexamethylene sulfone, trimethylene disulfone, tetramethylene disulfone, hexamethylene disulfone, sulfolane, 3-methylsulfolane, dimethyl sulfone, ethyl methyl sulfone, diethyl sulfone, methyl n-propyl sulfone, ethyl n-propyl sulfone, di-n-propyl sulfone, methyl isopropyl sulfone, ethyl isopropyl sulfone, diisopropyl sulfone, n-butyl methyl sulfone, n-butyl ethyl sulfone, t-butyl methyl sulfone, t-butyl ethyl sulfone, and the like. Among these, the sulfone compound represented by formula (3) is preferably sulfolane, 3-methylsulfolane, ethyl methyl sulfone, or ethyl isopropyl sulfone; more preferably sulfolane or 3-methylsulfolane; and even more preferably sulfolane.

When the compound represented by formula (2) and the compound represented by formula (3) are both used in step A, the sulfoxide compound and the sulfone compound are preferably at least one member selected from the group consisting of dimethylsulfoxide, sulfolane, 3-methylsulfolane, ethyl methyl sulfone, and ethyl isopropyl sulfone; more preferably at least one member selected from the group consisting of sulfolane, 3-methylsulfolane, ethyl methyl sulfone, and ethyl isopropyl sulfone; and particularly preferably contain at least sulfolane.

In step A, the sulfoxide compounds and the sulfone compounds can be used singly or in combination of two or more.

The sulfoxide compound and sulfone compound used in step A both can be obtained from commercially available products, or can be obtained by using known production methods or the like.

Reaction in Step A

In step A, at least one alkanesulfonic acid compound and sulfur trioxide ($SO_3$) are reacted in the presence of at least one member selected from the group consisting of a sulfoxide compound and a sulfone compound.

The total amount of the sulfoxide compound and sulfone compound used in the reaction of step A is preferably 0.1 mol or more, more preferably 0.2 mol or more, and even more preferably 0.3 mol or more, per mol of sulfur trioxide, because the yield of the object alkanedisulfonic acid compound tends to be high. Further, the total amount of the sulfoxide compound and sulfone compound used in the reaction of step A is preferably 10 mol or less, more preferably 8 mol or less, and even more preferably 6 mol or less, per mol of sulfur trioxide, in terms of being more economical.

The sulfoxide compound and sulfone compound used in step A may form complexes with sulfur trioxide depending on their types. For example, when the sulfone compound is sulfolane, it tends to form a complex with sulfur trioxide.

The amount of sulfur trioxide used in the reaction of step A is preferably 0.1 mol or more, more preferably 0.2 mol or more, and even more preferably 0.3 mol or more, per mol of the alkanesulfonic acid compound, because the yield of the object alkanedisulfonic acid compound tends to be high. Further, the amount of sulfur trioxide used in the reaction of step A is preferably 10 mol or less, more preferably 8 mol or less, and even more preferably 6 mol or less, per mol of the alkanesulfonic acid compound, in terms of being more economical. The phrase "per mol of the alkanesulfonic acid compound" as used herein means that when two or more alkanesulfonic acid compounds are used, the total amount thereof is 1 mol.

In the reaction of step A, for example, a raw material comprising the alkanesulfonic acid compound, sulfur trioxide, and at least one member selected from the group consisting of the sulfoxide compound and the sulfone compound is placed in a reaction vessel, and the reaction can be carried out in the reaction vessel while stirring the raw material. Alternatively, in the reaction of step A, the reaction can be carried out, for example, by placing a raw material comprising the alkanesulfonic acid compound and at least one member selected from the group consisting of the sulfoxide compound and the sulfone compound in a reaction vessel, and further adding sulfur trioxide while stirring the raw material. In this case, sulfur trioxide can be added in several times.

In the reaction of step A, a solvent can be used, if necessary. When a solvent is used, the amount thereof is not particularly limited. For example, the amount of solvent can be set to 1500 parts by mass or less, and preferably 1000 parts by mass or less, based on 100 parts by mass of the total amount of the alkanesulfonic acid compound.

When a solvent is used, usable solvents can be suitably selected within the range in which the effect of the present invention is not impaired. Examples of such solvents include hydrocarbon-based solvents, halogen-based solvents, ether-based solvents, ketone-based solvents, ester-based solvents, amide-based solvents, nitrile-based solvents, sulfoxide-based solvents, sulfone-based solvents, sulfuric acid, and the like. Examples of hydrocarbon-based solvents include toluene, xylene, monochlorobenzene, dichlorobenzene, trichlorobenzene, hexane, heptane, decane, and the like. Examples of halogen-based solvents include dichloromethane, 1,2-dichloroethane, and the like. Examples of ether-based solvents include diethyl ether, ethylene glycol dimethyl ether, diisopropyl ether, diphenyl ether, tetrahydrofuran, dioxane, methyl-tert-butyl ether, cyclopentyl methyl ether, and the like. Examples of ketone-based solvents include acetone, methyl ethyl ketone, methyl isobutyl ketone, and the like. Examples of ester-based solvents include ethyl acetate, butyl acetate, and the like. Examples of amide-based solvents include dimethylformamide, dimethylacetamide, N-methylpyrrolidone, and the like. Examples of nitrile-based solvents include acetonitrile and the like. Examples of sulfoxide-based solvents include dimethylsulfoxide and the like. Examples of sulfone-based solvents include ethyl methyl sulfone, ethyl isopropyl sulfone, sulfolane, 3-methylsulfolane, and the like.

When the compound represented by formula (2) or the compound represented by formula (3) is used in an excessive amount relative to sulfur trioxide ($SO_3$) in the reaction of step A, these compounds can substantially play the role of solvents. Specifically, when the sulfoxide compound represented by formula (2) is used in an excessive amount, the sulfoxide compound that is not consumed in the reaction plays the role of the reaction solvent of step A. In this case, the reaction solvent is, for example, a sulfoxide-based solvent mentioned above. Further, when the compound represented by formula (3) is used in an excessive amount, the sulfone compound that is not consumed in the reaction plays the role of the reaction solvent of step A. In this case, the reaction solvent is, for example, a sulfone-based solvent mentioned above.

When a solvent is used in the reaction of step A, the solvent preferably contains at least one member selected from the group consisting of the compound represented by formula (2) (sulfoxide compound) and the compound represented by formula (3) (sulfone compound); and more preferably the compound represented by formula (3) (sulfone compound). That is, in the reaction of step A, the compound represented by formula (2) (sulfoxide compound) and/or the compound represented by formula (3) (sulfone compound) are preferably used in excessive amounts, and the compound represented by formula (2) (sulfoxide compound) and/or the compound represented by formula (3) (sulfone compound) that are not consumed in the reaction are preferably used as solvents. In this case, the solvent is preferably sulfolane because the yield of the alkanedisulfonic acid compound tends to be higher.

When the solvent contains the compound represented by formula (2) (sulfoxide compound) and/or the compound represented by formula (3) (sulfone compound), the content thereof is 50 mass % or more, preferably 70 mass % or more, even more preferably 90 mass % or more, and particularly preferably 95 mass % or more, based on the entire mass of the solvent. The solvent may consist of the compound represented by formula (2) (sulfoxide compound) and/or the compound represented by formula (3) (sulfone compound).

The type of reaction vessel used in the reaction of step A is not particularly limited. For example, a wide range of known reaction vessels can be used.

The conditions of the reaction performed in step A are also not particularly limited. For example, the temperature of the reaction performed in step A is not particularly limited, and can be suitably set depending on the type and amount of raw material used and other conditions. For example, the reaction temperature can be set to 0 to 200° C., and because the yield of the object tends to be higher, preferably 50 to 180° C., more preferably 80 to 170° C., and even mover preferably 100 to 160° C. The reaction time can be suitably set depending on the reaction temperature, and can be set to about 1 to 48 hours, for example.

In the reaction of step A, the method of adjusting the reaction temperature is also not particularly limited. For example, the reaction vessel containing the raw material can be heated to set an appropriate reaction temperature.

The reaction of step A can be carried out under pressurized, depressurized, or atmospheric conditions. Further, the reaction of step A can also be carried out under an inert gas atmosphere, such as nitrogen or argon. The reaction can also be carried out while blowing an inert gas.

As a result of the reaction of step A, product A comprising the object alkanedisulfonic acid compound is obtained. The alkanedisulfonic acid compound is represented by the following formula (4):

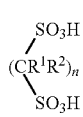

(4)

In formula (4), $R^1$, $R^2$, and n are respectively the same as $R^1$, $R^2$, and n in formula (1).

Specific examples of the alkanedisulfonic acid compound represented by formula (4) include methanedisulfonic acid ($R^1=R^2=H$, n=1), 1,1-ethanedisulfonic acid ($R^1=CH_3$, $R^2=H$, n=1), 1,2-ethanedisulfonic acid ($R^1=R^2=H$, n=2), 1,1-propanedisulfonic acid ($R^1=CH_2CH_3$, $R^2=H$, n=1), 1,2-propanedisulfonic acid ($R^1=CH_3$ and H, $R^2=H$, n=2), 1,3-propanedisulfonic acid ($R^1=R^2=H$, n=3), 2,2-propanedisulfonic acid ($R^1=R^2=CH_3$, n=1), 1,4-butanedisulfonic acid ($R^1=R^2=H$, n=4), and the like. Among these, the alkanedisulfonic acid compound represented by formula (4) is preferably methanedisulfonic acid. In this case, the production yield of methylene disulfonate tends to increase in the subsequent step B.

Product A produced in step A may contain unreacted raw materials and by-products in the reaction, in addition to the alkanedisulfonic acid compound. Further, when a solvent is used in the reaction of step A, product A is obtained in a state where the alkanedisulfonic acid compound is dissolved or precipitated in the solvent. As described above, when the compound represented by formula (2) or the compound represented by formula (3) is used as a solvent in an excessive amount relative to sulfur trioxide ($SO_3$), product A may contain these compounds as solvents.

Product A obtained by the reaction of step A can be used in the reaction of the subsequent step B after isolating the alkanedisulfonic acid compound by purification treatment or the like. Alternatively, reactant A can be used in the reaction of the subsequent step B without isolating the alkanedisulfonic acid compound from product A obtained by the reaction of step A. From the viewpoint that the entire production process tends to be simpler and less complicated, and that production efficiency tends to improve, it is preferable to use reactant A in step B without isolating the alkanedisulfonic acid compound from product A obtained by the reaction of step A. That is, product A comprising the alkanedisulfonic acid compound obtained in step A can be used as a raw material for producing a methylene disulfonate compound.

When the alkanedisulfonic acid compound is isolated from product A obtained in step A, for example, conventionally known purification and isolation operations can be used, and the method thereof is not particularly limited. For example, product A obtained after the reaction of step A can be extracted with a solvent or the like and washed, followed by crystallization, thereby isolating the alkanedisulfonic acid compound from product A obtained in step A.

In general, in the production of an alkanedisulfonic acid compound using sulfur trioxide, the reaction between sulfur trioxide and an alkanesulfonic acid compound is less likely to occur, and thus the yield of the alkanedisulfonic acid compound is low. In contrast, as in step A, when the reaction is carried out in the presence of at least one member selected from the group consisting of a sulfoxide compound and a sulfone compound, these compounds have the effect of effectively reacting sulfur trioxide with an alkanesulfonic acid compound. Therefore, the reaction between sulfur trioxide and the alkanesulfonic acid compound is likely to occur, which improves the yield of the alkanedisulfonic acid compound to be produced.

2. Step B In step B, reactant A obtained in step A and a formaldehyde compound are reacted in the presence of sulfur trioxide. As a result of this reaction, methylene disulfonate, which is the target compound, is produced. Specifically, step B is a step for producing a methylene disulfonate compound from the alkanedisulfonic acid compound in product A.

Formaldehyde Compound

Examples of the formaldehyde compound used in step B include paraformaldehyde, anhydrous formaldehyde, trioxane, acetalized formaldehyde (e.g., methylal), and the like. Anhydrous formaldehyde can be obtained, for example, by heating paraformaldehyde. Trioxane can be obtained, for example, by treating paraformaldehyde with acid. Among these, the formaldehyde compound used in step B is preferably at least one member selected from the group consisting of paraformaldehyde, anhydrous formaldehyde, trioxane, and methylal; more preferably at least one member selected from the group consisting of paraformaldehyde, anhydrous formaldehyde, and trioxane; and particularly preferably paraformaldehyde. In step B, the formaldehyde compounds can be used singly or in combination of two or more.

Reaction in Step B

The amount of the formaldehyde compound used in the reaction of step B is preferably 0.6 mol or more, more preferably 0.7 mol or more, and even more preferably 0.8 mol or more, per mol of the alkanedisulfonic acid compound, because the yield of the object methylene disulfonate compound tends to be high. Further, the amount of the formaldehyde compound used in the reaction of step B is preferably 10 mol or less, more preferably 7 mol or less, and even more preferably 5 mol or less, per mol of the alkanedisulfonic acid compound, in terms of being more economical.

The amount of sulfur trioxide used in the reaction of step B is preferably 0.1 mol or more, more preferably 0.2 mol or more, and even more preferably 0.3 mol or more, per mol of the alkanedisulfonic acid compound, because the yield of the object methylene disulfonate compound tends to be high. Further, the amount of sulfur trioxide used in the reaction of step B is preferably 10 mol or less, more preferably 8 mol or less, and even more preferably 6 mol or less, per mol of the alkanedisulfonic acid compound, in terms of being more economical.

In the reaction of step B, a dehydrating agent may be further used for the purpose of promoting the reaction. Examples of dehydrating agents include phosphorus pentoxide, phosphorus pentachloride, phosphorus oxychloride, thionyl chloride, acetyl chloride, acetic anhydride, aluminum chloride, and the like. Among these, phosphorus pentoxide is preferably used, in terms of reactivity. The dehydrating agents can be used singly or in combination of two or more.

The amount of the dehydrating agent used in the reaction of step B can be set to, for example, 0 to 10 mol, preferably 0 to 5.0 mol, and more preferably 0 to 3.0 mol, per mol of the alkanedisulfonic acid compound. The lower limit of this range is not particularly limited, and can be set to, for example, about 0.1, 0.5, or 1 mol.

In the reaction of step B, a solvent can be used, if necessary. When a solvent is used, the amount thereof is not particularly limited. For example, the amount of solvent can be set to 1500 parts by mass or less, and preferably 1000 parts by mass or less, based on 100 parts by mass of the total amount of the alkanedisulfonic acid compound. Further, when a solvent is used in step B, for example, the amount thereof can be set to 10 parts by mass or more based on 100 parts by mass of the total amount of the alkanedisulfonic acid compound.

When a solvent is used in the reaction of step B, the type of solvent can be suitably selected within the range in which the effect of the present invention is not impaired. Examples of such solvents include hydrocarbon-based solvents, ether-based solvents, ketone-based solvents, ester-based solvents, amide-based solvents, nitrile-based solvents, sulfoxide-based solvents, sulfone-based solvents, sulfuric acid, and the like. Examples of hydrocarbon-based solvents include toluene, xylene, monochlorobenzene, dichlorobenzene, trichlorobenzene, hexane, heptane, decane, and the like. Examples of ether-based solvents include diethyl ether, ethylene glycol dimethyl ether, diisopropyl ether, diphenyl ether, tetrahydrofuran, dioxane, methyl-tert-butyl ether, cyclopentyl methyl ether, and the like. Examples of ketone-based solvents include acetone, methyl ethyl ketone, methyl isobutyl ketone, and the like. Examples of ester-based solvents include ethyl acetate, butyl acetate, and the like. Examples of amide-based solvents include dimethylformamide, dimethylacetamide, N-methylpyrrolidone, and the like. Examples of nitrile-based solvents include acetonitrile and the like. Examples of sulfoxide-based solvents include dimethylsulfoxide and the like. Examples of sulfone-based solvents include ethyl methyl sulfone, ethyl isopropyl sulfone, sulfolane, 3-methylsulfolane, and the like.

Preferred as the solvent used in the reaction of step B among these are ether-based solvents, ketone-based solvents, ester-based solvents, amide-based solvents, nitrile-based solvents, sulfoxide-based solvents, sulfone-based solvents, and sulfuric acid; more preferred are sulfoxide-based solvents, sulfone-based solvents, and sulfuric acid; and even more preferred are sulfoxide-based solvents and sulfone-based solvents.

When a solvent is used in step B, the solvent may contain the compound represented by formula (2) and/or the compound represented by formula (3), which are used in excessive amounts in step A to function as solvents, as described above. Therefore, any new solvent is not additionally used in step B, and the compound represented by formula (2) and/or the compound represented by formula (3) used in excessive amounts in step A can be continuously used as reaction solvents in step B.

When a solvent is used in the reaction of step B, the solvent preferably contains the compound represented by formula (3) (sulfone compound), and the solvent is preferably sulfolane among these, because the yield of the alkanedisulfonic acid compound tends to be higher. When the solvent contains the compound represented by formula (3) (sulfone compound), the content thereof is 50 mass % or more, preferably 70 mass % or more, more preferably 90 mass % or more, and particularly preferably 95 mass % or more, based on the entire mass of the solvent. The solvent may consist of the compound represented by formula (3).

In the production method of the present invention, the reaction of step A and the reaction of step B are preferably performed in the presence of a solvent. In this case, the object methylene disulfonate compound can be obtained with a good yield. In particular, it is preferable to use a solvent containing the compound represented by formula (3) in the reaction of step A and the reaction of step B, and it is particularly preferable to use sulfolane as a solvent in the reaction of step A and the reaction of step B. In this case, the yield of the methylene disulfonate compound is improved, and no purification treatment is necessary after the reaction of step A, which further simplifies the production process.

The type of reaction vessel used in the reaction of step B is not particularly limited. For example, a wide range of known reaction vessels can be used.

The method of the reaction of step B is not particularly limited. For example, while stirring a raw material comprising product A comprising the alkanedisulfonic acid compound obtained in step A, sulfur trioxide, an optionally used dehydrating agent mentioned above, and an optionally used solvent mentioned above in a reaction vessel, a formaldehyde compound (e.g., paraformaldehyde) can be added to perform the reaction. Alternatively, while sufficiently stirring a raw material comprising the alkanedisulfonic acid compound obtained in step A, a formaldehyde compound, an optionally used dehydrating agent mentioned above, and an optionally used solvent mentioned above in a reaction vessel, sulfur trioxide can be added to perform the reaction. As still another method, while sufficiently stirring a raw material comprising a formaldehyde compound, sulfur trioxide, an optionally used dehydrating agent mentioned above, and an optionally used solvent mentioned above in a reaction vessel, product A comprising the alkanedisulfonic acid compound obtained in step A can be added to perform the reaction.

The conditions of the reaction performed in step B are also not particularly limited. For example, the temperature of the reaction performed in step B is not particularly limited, and can be suitably set depending on the type and amount of raw material used and other conditions. For example, the reaction temperature can be set to 0 to 200° C., and because the yield of the object tends to be higher, preferably 10 to 170° C., more preferably 20 to 160° C., and even mover preferably 40 to 160° C. Further, the reaction temperature can be adjusted in so-called multiple stages. After the reaction is carried out at a certain temperature for a certain period of time, the temperature can be further raised, and the reaction can be carried out. When the reaction temperature is adjusted in multiple stages, the reaction temperature can be adjusted in the range of 0 to 200° C.

The reaction time can be suitably set depending on the reaction temperature, and can be set to about 0.1 to 20 hours, for example.

In the reaction of step B, the method of adjusting the reaction temperature is also not particularly limited. For example, the reaction vessel containing the raw material used in step B can be heated to set an appropriate reaction temperature.

The reaction of step B can be carried out under pressurized, depressurized, or atmospheric conditions. Further, the reaction of step B can also be carried out under an inert gas atmosphere, such as nitrogen or argon. The reaction can also be carried out while blowing an inert gas.

As a result of the reaction of step B, product B comprising the object methylene disulfonate compound is obtained. The methylene disulfonate compound is represented by the following formula (5):

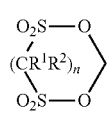

(5)

In formula (5), $R^1$, $R^2$, and n are respectively the same as $R^1$, $R^2$, and n in formula (1). That is, the methylene disulfonate compound represented by formula (5) can be determined depending on the type of alkanesulfonic acid compound used in step A.

Specific examples of the methylene disulfonate compound represented by formula (5) include methylene methane disulfonate ($R^1=R^2=H$, n=1), methylene 1,1-ethane disulfonate ($R^1=CH_3$, $R^2=H$, n=1), methylene 1,2-ethane disulfonate ($R^1=R^2=H$, n=2), methylene 1,1-propane disulfonate ($R^1=CH_2CH_3$, $R^2=H$, n=1), methylene 1,2-propane disulfonate ($R^1=CH_3$ and H, $R^2=H$, n=2), methylene 1,3-propane disulfonate ($R^1=R^2=H$, n=3), methylene 2,2-propane disulfonate ($R^1=CH_3$, $R^2=CH_3$, n=1), methylene 1,4-butane disulfonate ($R^1=R^2=H$, n=4), and the like.

Product B obtained in step B can be subjected to purification treatment or the like to isolate the methylene disulfonate compound. In this case, for example, conventionally known purification and isolation operations can be used, and the method thereof is not particularly limited. For example, product B obtained after the reaction of step B can be extracted with an organic solvent or the like and washed with water, followed by crystallization, thereby obtaining the methylene disulfonate compound. Alternatively, water or the like can be added to product B to decompose sulfur trioxide, followed by extraction with an organic solvent, water washing, etc., and further followed by crystallization in the same manner as described above, thereby obtaining the methylene disulfonate compound. Further, a poor solvent, such as water, can be added to product B to precipitate a crude product, which is then filtered, followed by recrystallization, thereby obtaining the methylene disulfonate compound.

Examples of the organic solvent in the purification treatment include methylene chloride, acetonitrile, and the like.

The present disclosure includes all of any combinations of the configuration requirements described in the present specification. Further, the various characteristics (properties, structures, functions, etc.) described for each embodiment of the present disclosure described above may be combined in any way in identifying the main subjects included in the present disclosure. That is, the present disclosure includes all the main subjects comprising various combinations of the characteristics that can be combined described in the present specification.

EXAMPLES

The present invention is described in more detail below with reference to Examples; however, the present invention is not limited to these Examples.

Example 1

In a four-necked flask equipped with a stirrer, a cooling tube, a thermometer, and a dropping funnel, 9.6 g (0.10 mol) of methanesulfonic acid, 10 g (0.085 mol) of sulfolane, and 16 g (0.20 mol) of sulfur trioxide were placed as raw materials. While stirring the raw materials in the flask, the temperature was raised to 150° C., and the reaction was continued at this temperature for 6 hours to thereby obtain reactant A (step A). An appropriate amount of the obtained reactant A was taken for ion chromatography analysis. Based on the area values of the peaks obtained in this analysis, the production yield of the product, i.e., methanedisulfonic acid represented by formula (4) (compound wherein $R^1$ and $R^2$ are hydrogen atoms, and n is 1), was calculated using the methanesulfonic acid placed as a reference. As a result, the production yield of the resulting methanedisulfonic acid was 74 mol %.

Subsequently, 12 g (0.15 mol) of sulfur trioxide was added to reactant A, and 3.6 g (0.11 mol as formaldehyde) of 91% paraformaldehyde was added under stirring at room temperature (25° C.). After completion of the addition, the temperature was raised to 55° C., and stirring was continued at this temperature for 3 hours to perform the reaction, thereby obtaining reactant B (step B). The production yield of methylene methane disulfonate in reactant B obtained by this reaction was 81 mol % based on the methanedisulfonic acid obtained in step A. The production yield was determined from the peak area values obtained by sampling the reaction liquid containing reactant B obtained by the reaction, followed by HPLC analysis (the same was used in the following examples).

After reactant B was cooled to 25° C., methylene chloride and water were added, followed by liquid separation, and the organic layer was taken out and washed with water. The obtained organic layer was concentrated, crystals precipitated therefrom were filtered off, and the obtained crystals were dried at 40° C. and 10 mmHg for 6 hours to thereby obtain 5.7 g of methylene methane disulfonate as a solid content. The yield of methylene methane disulfonate relative to the methanesulfonic acid used in step A was 30 mol %. It could be determined from the $^1$H-NMR analysis results shown below that the crystals were methylene methane disulfonate.

$^1$H-NMR (400 MHz, CD3CN) δ (ppm): 5.33 (s, 2H), 6.00 (s, 2H).

Example 2

In a four-necked flask equipped with a stirrer, a cooling tube, a thermometer, and a dropping funnel, 14.4 g (0.15 mol) of methanesulfonic acid and 15 g (0.13 mol) of sulfolane were placed as raw materials. While stirring the raw materials in the flask, the temperature was raised to 150° C., 12 g (0.15 mol) of sulfur trioxide was added dropwise at this temperature, and then stirring was continued for 5 hours to perform the reaction. Then, 12 g (0.15 mol) of sulfur trioxide was further added, and stirring was continued for 1 hour to thereby obtain reactant A (step A). An appropriate amount of the obtained reactant A was taken for ion chromatography analysis. Based on the area values of the peaks obtained in this analysis, the production yield of the product, i.e., methanedisulfonic acid represented by formula (4) (compound wherein $R^1$ and $R^2$ are hydrogen atoms, and n is 1), was calculated using the methanesulfonic acid placed as a reference. As a result, the production yield of the resulting methanedisulfonic acid was 70 mol.

Subsequently, 57 g (0.72 mol) of sulfur trioxide was added to reactant A, and 20 g (0.60 mol as formaldehyde) of 91% paraformaldehyde was added under stirring at room temperature (25° C.). After completion of the addition, the temperature was raised to 60° C., and stirring was continued at this temperature for 1 hour to perform the reaction. Then, the temperature was raised to 100° C., and stirring was performed for 2 hours to thereby obtain reactant B (step B). The production yield of methylene methane disulfonate in reactant B obtained by this reaction was 83 mol % based on the methanedisulfonic acid produced in step A.

Example 3

In a four-necked flask equipped with a stirrer, a cooling tube, a thermometer, and a dropping funnel, 14.4 g (0.15 mol) of methanesulfonic acid and 15 g (0.13 mol) of sulfolane were placed as raw materials. While stirring the raw materials in the flask, the temperature was raised to 150° C., 17 g (0.22 mol) of sulfur trioxide was added dropwise at this temperature, and then stirring was continued for 10 hours to perform the reaction. As a result, reactant A was obtained (step A). An appropriate amount of the obtained reactant A was taken for ion chromatography analysis. Based on the area values of the peaks obtained in this analysis, the production yield of the product, i.e., methanedisulfonic acid represented by formula (4) (compound wherein $R^1$ and $R^2$ are hydrogen atoms, and n is 1), was calculated using the methanesulfonic acid placed as a reference. As a result, the production yield of the resulting methanedisulfonic acid was 79 mol %.

Subsequently, 24 g (0.30 mol) of sulfur trioxide was added to reactant A, and 5 g (0.15 mol as formaldehyde) of 91% paraformaldehyde was added under stirring at room temperature (25° C.). After completion of the addition, the temperature was raised to 60° C., and stirring was continued at this temperature for 1.5 hours to perform the reaction. Then, the temperature was raised to 100° C., and stirring was performed for 1 hour to thereby obtain reactant B (step B). The production yield of methylene methane disulfonate in reactant B obtained by this reaction was 82 mol % based on the methanedisulfonic acid produced in step A.

Example 4

In a four-necked flask equipped with a stirrer, a cooling tube, a thermometer, and a dropping funnel, 9.6 g (0.10 mol) of methanesulfonic acid, 10 g (0.085 mol) of sulfolane, and 16 g (0.20 mol) of sulfur trioxide were placed as raw materials. While stirring the raw materials in the flask, the temperature was raised to 150° C., and stirring was continued for 10 hours to perform the reaction. As a result, reactant A was obtained (step A). An appropriate amount of the obtained reactant A was taken for ion chromatography analysis. Based on the area values of the peaks obtained in this analysis, the production yield of the product, i.e., methanedisulfonic acid represented by formula (4) (compound wherein $R^1$ and $R^2$ are hydrogen atoms, and n is 1), was calculated using the methanesulfonic acid placed as a reference. As a result, the production yield of the resulting methanedisulfonic acid was 78 mol %.

Subsequently, 12 g (0.15 mol) of sulfur trioxide was added to reactant A, and 4 g (0.12 mol as formaldehyde) of 91% paraformaldehyde was added under stirring at room temperature (25° C.). After completion of the addition, the temperature was raised to 55° C., and stirring was continued at this temperature for 4 hours to perform the reaction, thereby obtaining reactant B (step B). The production yield of methylene methane disulfonate in reactant B obtained by this reaction was 78 mol % based on the methanedisulfonic acid produced in step A.

Example 5

In a four-necked flask equipped with a stirrer, a cooling tube, a thermometer, and a dropping funnel, 4.8 g (0.05 mol) of methanesulfonic acid, 10 g (0.085 mol) of sulfolane, and 24 g (0.30 mol) of sulfur trioxide were placed as raw materials. While stirring the raw materials in the flask, the temperature was raised to 145° C., and stirring was continued for 11 hours to perform the reaction. As a result, reactant A was obtained (step A). An appropriate amount of the obtained reactant A was taken for ion chromatography analysis. Based on the area values of the peaks obtained in this analysis, the production yield of the product, i.e., methanedisulfonic acid represented by formula (4) (compound wherein $R^1$ and $R^2$ are hydrogen atoms, and n is 1), was calculated using the methanesulfonic acid placed as a reference. As a result, the production yield of the resulting methanedisulfonic acid was 58 mol %.

Subsequently, 14 g (0.17 mol) of sulfur trioxide was added to reactant A, and 6 g (0.18 mol as formaldehyde) of 91% paraformaldehyde was added under stirring at room temperature (25° C.). After completion of the addition, the temperature was raised to 55° C., and stirring was continued at this temperature for 1 hour to perform the reaction. Then, the temperature was raised to 100° C., and stirring was performed for 2 hours to thereby obtain reactant B (step B). The production yield of methylene methane disulfonate in reactant B obtained by this reaction was 84 mol % based on the methanedisulfonic acid produced in step A.

The above results revealed that according to the production methods performed in the Examples, the presence of steps A and B allowed the production of methylene disulfonate compounds easily and inexpensively, and that it was possible to produce methylene disulfonate compounds using fewer raw materials. Therefore, the production method according to the present invention is also industrially advantageous.

The invention claimed is:
1. A method for producing a methylene disulfonate compound, comprising:
  step A of reacting at least one alkanesulfonic acid compound and sulfur trioxide in the presence of sulfolane to thereby obtain reactant A comprising an alkanedisulfonic acid compound, and
  step B of reacting reactant A obtained in step A and a formaldehyde compound in the presence of sulfur trioxide and sulfolane to thereby obtain a methylene disulfonate compound;
  the amount of sulfolane in step A being 0.1 mol or more and 10 mol or less per mol of sulfur trioxide,
  the amount of sulfur trioxide added in step B being 2.0 mol or more and 10 mol or less per mol of the alkanedisulfonic acid compound;

the alkanesulfonic acid compound being represented by the following formula (1):

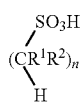 (1)

wherein in formula (1), $R^1$ and $R^2$ are the same or different, and each is a $C_{1-4}$ alkyl group optionally substituted with a halogen atom, or a hydrogen atom; and n is an integer of 1 to 4; when n is an integer of 2 to 4, n-number of $R^1$ may be the same or different, and n-number of $R^2$ may be the same or different;

the alkanedisulfonic acid compound being represented by the following formula (4):

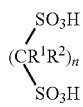 (4)

wherein in formula (4), $R^1$, $R^2$, and n are respectively the same as $R^1$, $R^2$, and n in formula (1); and the methylene disulfonate compound being represented by the following formula (5):

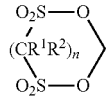 (5)

wherein in formula (5), $R^1$, $R^2$, and n are respectively the same as $R^1$, $R^2$, and n in formula (1).

2. The method for producing a methylene disulfonate compound according to claim 1, wherein reactant A obtained in step A is used in step B without isolating the alkanedisulfonic acid compound from reactant A.

3. The method for producing a methylene disulfonate compound according to claim 1, wherein the reaction of step A and the reaction of step B are performed in the presence of a solvent.

4. The method for producing a methylene disulfonate compound according to claim 1, wherein the formaldehyde compound is at least one member selected from the group consisting of paraformaldehyde, anhydrous formaldehyde, trioxane, and methylal.

* * * * *